(12) United States Patent
Nakada et al.

(10) Patent No.: US 6,329,560 B2
(45) Date of Patent: Dec. 11, 2001

(54) METHOD FOR PRODUCING HYDROGEN-CONTAINING FLUORINATED HYDROCARBON

(75) Inventors: Tatsuo Nakada; Noriaki Shibata; Takashi Shibanuma, all of Osaka (JP)

(73) Assignee: Daikin Industries, Ltd., Osaka-fu (JP)

( * ) Notice: Subject to any disclaimer, the term of this patent is extended or adjusted under 35 U.S.C. 154(b) by 0 days.

(21) Appl. No.: 09/758,420

(22) Filed: Jan. 12, 2001

(30) Foreign Application Priority Data

Jan. 12, 2000 (JP) .................................................. 12-003519

(51) Int. Cl.$^7$ .................................................. C07C 17/08
(52) U.S. Cl. .......................... 570/165; 570/166; 570/167; 570/168; 570/169
(58) Field of Search .................................. 570/165, 166, 570/167, 168, 169

(56) References Cited

FOREIGN PATENT DOCUMENTS

| | | |
|---|---|---|
| 0823412A1 | 2/1998 | (EP) . |
| 7233102A | 9/1995 | (JP) . |
| 8501551A | 2/1996 | (JP) . |
| 10120602A | 5/1998 | (JP) . |
| 9406554A1 | 3/1994 | (WO) . |
| 9926720A1 | 6/1999 | (WO) . |

*Primary Examiner*—Alan Siegel
(74) *Attorney, Agent, or Firm*—Birch, Stewart, Kolasch & Birch, LLP (57) ABSTRACT

A method for producing a hydrogen-containing fluorinated hydrocarbon includes supplying HF to a gap between an inner reactor made of a material resistant to the reaction and an outer container made of a material resistant to HF; supplying HF to the inner reactor; supplying a halogenated hydrocarbon selected from a chlorinated alkene and a hydrogen-containing chlorinated alkane to the inner reactor; and reacting HF with halogenated hydrocarbon in the presence of a fluorination catalyst in the inner reactor to obtain the reaction product containing the hydrogen-containing fluorinated hydrocarbon.

19 Claims, 3 Drawing Sheets

METHOD FOR PRODUCING HYDROGEN-CONTAINING FLUORINATED HYDROCARBON

CROSS-REFERENCE TO RELATED APPLICATION

The present application claims a priority under 35 U.S.C. §119 to an Japanese Patent Application No. 2000-3519, filed on Jan. 12, 2000, entitled "METHOD FOR PRODUCING HYDROGEN-CONTAINING FLUORINATED HYDROCARBON". The contents of that application are incorporated herein by reference in their entirety.

BACKGROUND OF THE INVENTION

1. Field of the Invention

The present invention relates to a method for producing a hydrogen-containing fluorinated hydrocarbon and an apparatus therefor. It is to be noted that throughout the present specification, the term "hydrogen-containing fluorinated hydrocarbon" means a compound as a hydrocarbon of which a part (i.e. one or more) of hydrogen atoms is substituted by a fluorine atom(s) and which contains at least one hydrogen atom. The hydrogen-containing fluorinated hydrocarbon may or may not contain a chlorine atom(s). In terms of example, the hydrogen-containing fluorinated hydrocarbon includes a hydrogen-containing fluorinated alkane and a hydrogen-containing fluorinated alkene and the like.

2. Description of the Related Art

A chlorofluorocarbon generally known as a flon gas has been used for a foaming agent, a cleaning agent, and a refrigerant owing to its stable and thermal properties. The chlorofluorocarbon is a simple alkane such as methane or ethane of which all of hydrogen atoms are substituted by a chlorine atom(s) and/or a fluorine atom(s). Recently, such a chlorofluorocarbon has been subjected to regulation since the chlorofluorocarbon has been found to have a property of damaging the ozone layer.

Thus, demand of a hydrogen-containing fluorinated hydrocarbon which scarcely affects or does not affect the ozone layer has been increased and the development of such hydrogen-containing fluorinated hydrocarbon has been undertaken. The hydrogen-containing fluorinated hydrocarbon includes a hydrogen-containing fluorinated alkane, for example, 2,2-dichloro-1,1,1-trifluoroethane (also called as HCFC-123) and 1,1,1,3,3-pentafluoropropane (also called as HFC-245fa). HCFC-123 is a useful compound as a refrigerant for a turbo refrigerator or as an intermediate raw material for the production of 2-chloro-1,1,1,2-tetrafluoroethane (also called as HCFC-124) and pentafluoroethane (also called as HCFC-125). Further, HFC-245fa is a useful compound for a foaming agent which is not likely to damage the ozone layer.

In order to produce such a hydrogen-containing fluorinated hydrocarbon, the conventional method for producing a chlorofluorocarbon containing no hydrogen atom such as trichlorofluoromethane (also called as CFC-11), dichlorodifluoromethane (also called as CFC-12), and 1,1,2-trichlorotrifluoroethane (also called as CFC-113) can be applicable. As the conventional method for producing the chlorofluorocarbon, a method by reacting a chlorinated alkene and/or a chlorinated alkane with a hydrogen fluoride in the presence of a fluorination catalyst to produce the chlorofluorocarbon is known.

In the foregoing method for producing the chlorofluorocarbon, a reaction mixture has a corrosive property owing to the interaction of the fluorination catalyst and hydrogen fluoride. Upon the application of such a method to the production of the hydrogen-containing fluorinated hydrocarbon, reaction conditions result is a reaction mixture which shows an extremely intense corrosive property. Consequently, if a conventional and commonly used apparatus material, e.g. a stainless steel based material, is used for a reactor in which a fluorination reaction is to be carried out to produce the hydrogen-containing fluorinated hydrocarbon, the reactor will be severely corroded and worn-out. Therefore, there occur problems of a shorter lifetime of the reactor and an increased facility cost including a cost of the reactor.

Taking the high corrosive property of the reaction mixture into consideration, it is suggested that the following reactors are employed for the fluorination reaction:

(1) A reactor made of a composite material which contains at least one corrosion resistant metal selected from a group consisting of gold, platinum, palladium, molybdenum, rhenium, and tungsten (see Japanese Patent Kohyo Publication No. 8-501551);

(2) A reactor made of a fluoro resin or lined with a fluoro resin (see Japanese Patent Kokai Publication No. 7-233102);

(3) A reactor having an inner surface made of a corrosion resistant metal material containing aluminum (see Japanese Patent Kokai Publication No. 10-120602); and (4) A reactor installed in the inside of a container made of a metal material and at least of which inner surface is coated with a fluoro resin (see WO 99/26720).

However, all of the above described reactors (1) to (4) have defects and they are not necessarily optimum for the reactor to be employed for producing the hydrogen-containing fluorinated hydrocarbon. Particularly, among the corrosion resistant metals to be used for the reactor (1), gold, platinum, palladium and rhenium are too expensive to be used for producing a large scale reactor. Molybdenum and tungsten have a disadvantage of insufficient mechanical strength since welded parts of such metals are very brittle on account of welding heat and a trace amount of a contaminant which is introduced into the parts on welding. In addition, molybdenum and tungsten are inherently hard and brittle metal materials, and thus have inferior workability. Therefore, it is substantially impossible to form an industrial scale reactor employing these materials.

In the case of using a resin material like as in the reactors (2) and (4), since the resin materials generally have low thermal conductivity as compared with metal materials, the resin materials make it very difficult to sufficiently transfer a necessary quantity of heat from outside of the reactor to the inside of the reactor in order to gasify a reaction product, and especially in the case of using such a reactor having a large capacity, it is difficult to control a reaction temperature.

In the case of the reactor (3), though it has high corrosion resistance in a water-free condition, corrosion considerably proceeds even when only a small amount of water is present in the reaction mixture, so that it makes maintenance of the reactor extremely difficult, for example, water-washing which may leave water in the reactor can not be employed for periodic maintenance.

SUMMARY OF THE INVENTION

Hence, it is an object of the present invention to provide a new and more economical method for producing a hydrogen-containing fluorinated hydrocarbon in which a reaction mixture containing the hydrogen-containing fluorinated hydrocarbon as a reaction product is produced by reacting hydrogen fluoride and one or more of halogenated hydrocarbons as raw materials in the presence of a fluorination catalyst, whereby at least one of the foregoing technological problems are alleviated. It is another object to provide a reaction apparatus which is used for such a method.

According to the present invention, there is provided a method for producing a hydrogen-containing fluorinated hydrocarbon (or a hydrogen-containing fluorohydrocarbon) in which hydrogen fluoride as a reaction raw material and at least one halogenated hydrocarbon as a reaction raw materials selected from a group consisting of a chlorinated alkene and a hydrogen-containing chlorinated alkane are reacted in the presence of a fluorination catalyst so as to obtain a reaction mixture comprising a reaction product which comprises the hydrogen-containing fluorinated hydrocarbon, which method comprises the steps of:

(a) supplying one of the reaction raw material (it may be also called as the first reaction raw material) to a gap between an inner reactor made of a material (for example, a certain metal material) which is substantially resistant to the reaction and an outer container made of a material (for example, another certain metal material which may be the same as said certain metal material) which is substantially resistant to at least said one of the reaction raw materials and which is installed outside the inner reactor;

(b) supplying said one of the reaction raw materials (or the first reaction raw material) to the inner reactor;

(c) supplying the other reaction raw material (it may be also called as the second reaction raw material) to the inner reactor; and (d) reacting said one of the reaction raw materials (or the first reaction raw material) with the other reaction raw material (or the second reaction raw material) in the presence of the fluorination catalyst in the inner reactor so as to obtain the reaction product comprising the hydrogen-containing fluorinated hydrocarbon. According to the present invention, the foregoing object is achieved. In the method of the present invention, the first reaction raw material may be supplied to the inner reactor, for example, through the gap containing the first reaction raw material or directly from a supply source of the first reaction raw material, which will be explained later with reference to FIG. 1.

DETAILED DESCRIPTION OF THE INVENTION

In one embodiment of the present invention, the first reaction raw material or said one of the reaction raw materials may be hydrogen fluoride and the second or said the other reaction raw material may be at least one halogenated hydrocarbon. In other embodiment of the present invention, the first reaction raw material or said one of the reaction raw materials may be at least one halogenated hydrocarbon and the second or said the other reaction raw material may be hydrogen fluoride.

Concretely, one embodiment of the method according to the present invention may comprise: (a) supplying hydrogen fluoride to the gap between the inner reactor made of the material which is substantially resistant to the reaction and the outer container made of the material which is substantially resistant to at least hydrogen fluoride and which is installed outside the inner reactor; (b) supplying hydrogen fluoride to the inner reactor; (c) supplying the at least one halogenated hydrocarbon to the inner reactor; and (d) reacting hydrogen fluoride with the at least one halogenated hydrocarbon in the presence of the fluorination catalyst in the inner reactor so as to obtain the reaction product comprising the hydrogen-containing fluorinated hydrocarbon.

Other embodiment of the method according to the present invention may comprise: (a) supplying the at least one halogenated hydrocarbon to the gap between the inner reactor made of the material which is substantially resistant to the reaction and the outer container made of the material which is substantially resistant to at least the at least one halogenated hydrocarbon and which is installed outside the inner reactor; (b) supplying the at least one halogenated hydrocarbon to the inner reactor; (c) supplying hydrogen fluoride to the inner reactor; and (d) reacting hydrogen fluoride with the at least one halogenated hydrocarbon in the presence of the fluorination catalyst in the inner reactor so as to obtain the reaction product comprising the hydrogen-containing fluorinated hydrocarbon.

According to the present invention, the reaction mixture which is highly corrosive (that is, a liquid mixture containing the unreacted raw materials, the catalyst, and the reaction product) is held in the inner reactor. Even if a part of the reaction mixture leaks into the gap between the inner reactor and the outer container, the corrosion due to such reaction mixture is alleviated because of dilution with the first reaction raw material which is held in the gap. Consequently, the inner reactor is not required to have tight sealing against leakage of the reaction mixture into the gap and can be manufactured without complicated work, so that the material for the inner reactor can be selected from materials which are substantially resistant to the reaction regardless of it's workability. For example, even a metal material which has less workability and with which it is difficult to form a sealed portion by welding or other method may be employed as a material for the inner reactor as long as the material is substantially resistant to the reaction.

Further, the gap between the inner reactor and the outer container may be kept at a higher pressure than the pressure in the inside of the inner reactor. In this case, it is unnecessary to adjust the pressure in the gap depending on the absolute pressure of the inner reactor as long as there exists a positive pressure difference in the gap in relation to the inner reactor. By keeping the positive pressure difference in the gap in relation to the inner reactor, the leakage of the reaction mixture held in the inner reactor into the gap can be suppressed. Also, undesirable vaporization of the raw material existing in the gap can be suppressed.

In the present invention, "the material which is substantially resistant to the reaction" means a material of which quantity deteriorated by corrosion (i.e. corrosion quantity) during the reaction is allowable in the case where the above described fluorination reaction is carried out using the material for the reactor in an industrial production scale.

Such material can easily be selected by those skilled in the art, for example, by exposing test pieces of intended materials to expected reaction conditions for conducting the method of the present invention, and measuring corrosion quantities.

In one embodiment of the present invention, the material which is substantially resistant to the reaction, i.e. the material for the inner reactor, is a corrosion resistant metal material which contains one or more metals selected from a group consisting of molybdenum and tungsten. In terms of example, such material is an alloy material which contains Mo or W and which further contains other component. Further, some of high melting point metals which have high corrosion resistance can also be used, and for example Mo and W may be used.

Since the inner reactor is not required to have tight sealing as described above, it can be easily manufactured using a commercially available plate material by pressure welding or mechanical fixation by, for example, bolts and nuts.

Further, according to the present invention, since the inner reactor is disposed inside the outer container, a pressure difference between the reaction pressure and the ambient pressure is substantially applied to the outer container and scarcely applied to the inner reactor. Consequently, the inner reactor is not necessary to have high pressure resistance and a wall thickness of the inner reactor can be made smaller.

Furthermore, according to the present invention, the highly corrosive reaction mixture is held in the inner reactor and the outer container is not exposed to the highly corrosive reaction mixture. Consequently, the outer container is not required to be highly corrosion resistant and can be made of any material which is substantially resistant to the first reaction raw material which is held in the gap and contact with the outer container. Therefore, a material for the outer container can be selected from materials having good workability. It is to be noted that similarly to the above described material which is substantially resistant to the first reaction raw material, "the material which is substantially resistant to at least said one of the reaction raw materials", i.e. "the material which is substantially resistant to at least the first reaction raw material", means a material of which corrosion quantity is allowable in the case where said one of the reaction raw materials (i.e. the first reaction raw material) is held in the gap in an industrial production scale. Such materials can easily be selected by those skilled in the art, for example, by exposing test pieces of intended materials to expected reaction conditions for conducting the present invention, and measuring corrosion quantities.

Preferably, the material which is substantially resistant to the first reaction raw material, i.e. the material for the outer container, can be metal material such as nickel based alloys (e.g. Hostelloy (trade name) materials, Inconel (trade name) materials, and Monel (trade name) materials) stainless based materials, iron, and the likes. The metal materials have high thermal conductivity and therefore they are advantageous in that the quantity of heat necessary to withdraw the hydrogen-containing fluorinated hydrocarbon in a gas phase state, which is produced by the fluorination reaction, can sufficiently be supplied from the outside through the outer container and that the reaction temperature is easily controlled.

The method according to the present invention is applicable to either a continuous process or a batch process. Concretely, in the case of the batch process, (i) while the first reaction raw material being kept in the gap, both of the first and second reaction raw materials are supplied to the inner reactor and the fluorination reaction is carried out in the presence of the fluorination catalyst. On the other hand, in the case of the continuous process, while the first reaction raw material is kept in the gap, both or either one of the first and second reaction raw materials is continuously supplied to the inner reactor and the fluorination reaction is carried out in the presence of the fluorination catalyst. In the case of the continuous process, the following two methods may be carried out in order to continuously supply the first reaction raw material to the inner reactor: (ii) a method in which the first reaction raw material is continuously supplied to the inner reactor directly (not by way of the gap) from the outside of the reaction apparatus (in this case, the first reaction raw material in the gap is kept as it is); and (iii) a method in which the first reaction raw material held in the gap is continuously supplied to the inner reactor and the first reaction raw material continuously supplied to the gap in order to refill a decreased amount of the first reaction raw material held in the gap because of the continuous supply to the inner reactor.

According to the present invention, when the inner reactor is not completely sealed and a part of the reaction mixture leaks into the gap from the inner reactor, the part of the reaction mixture leaking into the gap from the inner reactor is diluted with the first reaction material held in the gap so that the corrosive property of the reaction mixture is lowered in the gap preferably to the level at which corrosive property does not substantially affects the material of the outer container. However, in the case where the present invention is performed by employing the foregoing methods (i) or (ii), a longer operation duration leads to gradual accumulation of the reaction mixture leaking out of the inner reactor in the liquid held in the gap, and the corrosive property of the liquid is therefore becomes strong. Hence, it is preferable to replace, if necessary, at least a part of the liquid in the gap with the first fresh reaction raw material. On the contrary, in the case of the foregoing method (iii), the liquid held in the gap does not have to be replaced by appropriately selecting the reaction conditions and the quantity of the reaction raw material to be supplied to the gap.

In a preferable embodiment of a method of the present invention, by employing the foregoing method (iii), the above described step (a) of supplying the first reaction raw material to the gap is continuously carried out, and the above described step (b) of supplying the first reaction raw material from the gap to the inner reactor is continuously carried out by continuously supplying to the inner reactor the first reaction raw material which is supplied to the gap. In this embodiment, the reaction mixture which has leaked into the gap can be returned, thereafter, to the inner reactor. The supply of the first reaction raw material, which is supplied to the gap, to the inner reactor can be carried out by an overflow manner, which will be described later with reference to FIG. 1. Alternatively, the first reaction raw material can be transferred to the inner reactor from the gap using a pump. In this case, one or more valves may be used if necessary.

Furthermore, the method of the present invention may further comprise the step of heating the reaction mixture and taking out a gasified fraction containing the reaction product. By means of the further step, the reaction product can selectively be taken out of the reaction mixture.

The fluorination catalyst which is employed in the present invention is a halide compound of one or more elements selected from a group consisting of antimony, niobium, and tantalum, and preferably the catalyst is a chloride, a fluoride, or a chloro-fluoride. The fluorination catalyst may be a mixture of two or more halides of different elements and/or different halogens. The fluorination catalyst may further contain an antimony compound such as $SbF_3$ with different valences and/or halides of titanium and/or tin. The antimony compound includes various compounds of which antimony valences are different. The fluorination catalyst is more preferably one or more compounds selected from $SbF_5$, $SbCl_5$, $SbCl_2F_3$, $NbClF_4$, $NbF_5$, $TaCl_5$, $TaF_5$, and $TaClF_4$.

As the reaction raw material, one or more halogenated hydrocarbons selected from a group consisting of a chlorinated alkene and a hydrogen-containing chlorinated alkane. The term "a chlorinated alkene" employed in the present specification means an alkene at least one of which hydrogen atom is substituted with a chlorine atom and which may or may not contain a hydrogen atom and may or may not contain a fluorine atom. The term "a hydrogen-containing chlorinated alkane" means a saturated hydrocarbon a part of which (or at least one of which) hydrogen atoms is substituted with a chlorine atom and which contains at least one hydrogen atom and which may or may not contain a fluorine atom. The chlorinated alkene and hydrogen-containing chlorinated alkane contain preferably 1 to 6 carbon atoms and more preferably 1 to 4 carbon atoms. In the present specification, it should be understood that the chlorinated alkene and the hydrogen-containing chlorinated alkane include a partly fluorinated derivative of these compounds. The term "a partly fluorinated compound" means a compound a part (but not all) of which chlorine atoms is substituted with a fluorine atom.

Concretely, the chlorinated alkene preferably includes a chlorinated ethylene (more preferably tetrachloroethylene, trichloroethylene), a chlorinated propene, a chlorinated butene and a partly fluorinated compounds of these alkenes. The hydrogen-containing chlorinated alkane preferably includes a hydrogen-containing chlorinated methane (more preferably dichloromethane), a hydrogen-containing chlorinated ethane, a hydrogen-containing chlorinated propane, and a partly fluorinated compounds of these alkanes.

The chlorinated ethylene can be expressed by the following general formula (1):

(wherein a, b, and c are integers satisfying a+b+c=4; a≧0; b≧0, and c≧1).

The hydrogen-containing chlorinated methane can be expressed by the following general formula (2):

(wherein d, e, and f are integers satisfying d+e+f=4; d≧1; e≧0, and f≧1).

The hydrogen-containing chlorinated ethane can be expressed by the following general formula (3):

(wherein g, h, and i are integers satisfying g+h+i=6; g≧1; h≧0, and i≧1).

The hydrogen-containing chlorinated propane can be expressed by the following general formula (4):

(wherein j, k, and l are integers satisfying j+k+l=8; j≧1; k≧0, and l≧1).

The chlorinated propene can be expressed by the following general formula (5):

(wherein m, n, and o are integers satisfying m+n+o=6; m≧0; n≧0, and o≧1).

The chlorinated butadiene can be expressed by the following general formula (6):

(wherein p, q, and r are integers satisfying p+q+r=6; p≧0; q≧0 and r≧1).

The hydrogen-containing fluorinated hydrocarbon as an aimed product is a compound having at least one hydrogen atom obtained by substitution of a part or all of chlorine atoms of a halogenated hydrocarbon (i.e. a starting reaction raw material) with a fluorine atom(s), and in the case wherein the halogenated hydrocarbon is the chlorinated alkene, optionally and. further by addition reaction of a fluorine atom and a hydrogen atom to at least one double bond of the chlorinated alkene to decrease the number of the double bonds. Consequently, the aimed product produced by the fluorination reaction differs depending on the halogenated hydrocarbon as the starting raw material. Combinations of the starting raw materials and the desirable aimed product are as follows.

In the case where the halogenated hydrocarbon as the reaction raw material (i.e. the starting raw material) is the chlorinated ethylene expressed by the foregoing general formula (1), the hydrogen-containing fluorinated hydrocarbon which is preferable as the aimed product is a hydrogen-containing fluorinated ethane expressed by the following general formula (7):

(wherein a, b, c and w are integers satisfying a+b+c=4; a≧0; b≧0, c≧1, and 0≦w≦c). Particularly, the preferable combinations of the starting raw material/the aimed product, that is, the halogenated hydrocarbon/the hydrogen-containing fluorinated hydrocarbon in this case are tetrachloroethylene/2,2-dichloro-1,1,1-trifluoroethane; trichloroethylene/2-chloro-1,1,1-trifluoroethane; vinylidene chloride/1,1,1-trifluoroethane; vinyl chloride/1,1-difluoroethane; 1,1,1-trichloroethane/1,1,1-trifluoroethane; and the like.

In the case where the halogenated hydrocarbon as the reaction raw material (i.e. the starting raw material) is the hydrogen-containing chlorinated methane expressed by the foregoing general formula (2), the hydrogen-containing fluorinated hydrocarbon which is preferable as the aimed product is a hydrogen-containing fluorinated methane expressed by the following general formula (8):

(wherein d, e, f and x are integers satisfying d+e+f=4; d≧1; e≧0, f≧1, and 1≦x≦f). Particularly, the preferable combinations of the halogenated hydrocarbon/the hydrogen-containing fluorinated hydrocarbon in this case are dichloromethane/difluoromethane and the like.

In the case where the halogenated hydrocarbon as the reaction raw material (i.e. the starting raw material) is the hydrogen-containing chlorinated ethane expressed by the foregoing general formula (3), the hydrogen-containing fluorinated hydrocarbon preferable as the aimed product is a hydrogen-containing fluorinated ethane expressed by the following general formula (9):

(wherein g, h, i and y are integers satisfying g+h+i=6; g≧1; h≧0, i≧1, and 1≦y≦i). Particularly, the preferable combinations of the halogenated hydrocarbon/the hydrogen-containing fluorinated hydrocarbon in this case are 1,1,1,2-tetrachloroethane/1,1,1-trifluoro-2-chloroethane and the like.

In the case where the halogenated hydrocarbon as the reaction raw material (i.e. a starting raw material) is the hydrogen-containing chlorinated propane expressed by the foregoing general formula (4), the hydrogen-containing fluorinated hydrocarbon preferable as the aimed product is a hydrogen-containing fluorinated propane expressed by the following general formula (10):

$$C_3H_jF_{k+z}Cl_{l-z} \qquad (10)$$

(wherein j, k, l and z are integers satisfying j+k+l=8; j≧1; k≧0, l≧1, and 1≦z≦l). Particularly, the preferable combinations of the halogenated hydrocarbon/the hydrogen-containing fluorinated hydrocarbon in this case are one or more substituted propanes selected from 1,1,1,3,3-pentachloropropane and a partially fluorinated compound thereof/1,1,1,3,3-pentafluoropropane and the like.

The partially fluorinated compound of 1,1,1,3,3-pentachloropropane means a compound formed by partially substituting a part of chlorine atoms of 1,1,1,3,3-pentachloropropane with a fluorine atom(s). Examples of such a compound include 1,1,3,3-tetrachloro-1-fluoropropane, 1,3,3-trichloro-1,1-difluoropropane, 3,3-dichloro-1,1,1-trifluoropropane, 3-chloro-1,1,1,3-tetrafluoropropane and the like.

In the case where the halogenated hydrocarbon as the reaction raw material (i.e. the starting raw material) is the chlorinated propene expressed by the foregoing general formula (5), the hydrogen-containing fluorinated hydrocarbon preferable as an aimed product is a hydrogen-containing fluoropropane expressed by the following general formula (11):

$$C_3H_{m+1}F_{n+u+1}Cl_{o-u} \qquad (11)$$

(wherein m, n, o and u are integers satisfying m+n+o=6; m≧0; n≧0, o≧1, and 0≦u≦o). Particularly, the preferable combinations of the halogenated hydrocarbon/the hydrogen-containing fluorinated hydrocarbon in this case are one or more substituted propenes selected from 1,1,1,2,3,3-hexachloropropene and partially fluorinated compounds thereof/2,3-dichloro-1,1,1,3,3-pentafluoropropane and the like.

The partially fluorinated compounds of 1,1,1,2,3,3-hexachloropropene mean compounds produced by partially substituting a part of chlorine atoms with a fluorine atom(s). Examples of such a compound include 2,3,3-trichloro-1,1,1-trifluorpropene, 1,2,3,3-tetrachloro-1,1-difluoropropene, 1,1,2,3,3-pentachloro-1-fluoropropene, and the like.

In the case where the halogenated hydrocarbon as the reaction raw material (i.e. the starting raw material) is the chlorinated butadiene expressed by the foregoing general formula (6), the hydrogen-containing fluorinated hydrocarbon preferable as the aimed product is a hydrogen-containing fluorinated butane expressed by the following general formula (12):

$$C_4H_{p+1}F_{q+v+1}Cl_{r-v} \qquad (12)$$

(wherein p, q, r and v are integers satisfying p+q+r=6; p≧0; q≧0, r≧1, and 0≦v≦r). Particularly, the preferable combinations of the halogenated hydrocarbon/the hydrogen-containing flourinated hydrocarbon in this case are 1,1,2,3,4,4-hexachlorobutadiene/2-chloro-1,1,1,4,4,4-hexafluorobutene and the like.

The halogenated hydrocarbon and hydrogen fluoride (i.e. the reaction raw materials) and the fluorination catalyst may be used in any proper amounts, respectively. A molar ratio of hydrogen fluoride to the halogenated hydrocarbon to be supplied both of which are as the reaction raw materials, except an amount of the reaction raw material existing in the gap between the outer container and the inner reactor (e.g. a part of hydrogen fluoride), is preferably controlled to be a stoichiometric molar ratio or higher. It is more preferable that hydrogen fluoride is present to be in an excess molar ratio. In general, while taking the efficiency of the reactor and the loss of unreacted hydrogen fluoride upon the recovery thereof into account, it is preferable to supply the reaction raw materials in the molar ratio of hydrogen fluoride to the halogenated hydrocarbon within the range from 1 to 10, and especially from 1 to 5.

The step (d) described above (which is also referred to as "a fluorination reaction step") proceeds in a liquid phase and is preferably carried out under the condition where at least said one (or the first) reaction raw material to be supplied to the gap is in a liquid state. This fluorination reaction is generally carried out in a normal or pressurized pressure. The reaction pressure, that is, the pressure in the inside of the reaction apparatus is preferably 0 to 20 kgf/cm² (0 to 1.96 MPa) of a gauge pressure, and more preferably 5 to 15 kgf/cm² (0.49 to 1.47 MPa) of a gauge pressure. The reaction temperature, that is, the temperature of the reaction mixture is preferably 0 to 175° C., and more preferably 20 to 120° C. Those reaction pressure ranges and temperature ranges are only examples, and the present invention is not intended to be limited to the foregoing exemplified ranges.

The fluorination reaction if the step (d) is, in general, carried out using the reaction raw materials and/or the reaction product as a reaction solvent. In order to obtain the aimed product at a high selectivity, hydrogen fluoride which is one of the reaction raw materials is especially preferably used as the reaction solvent.

In another aspect, the present invention provides a reaction apparatus comprising an inner reactor for carrying out a reaction of one (or a first) reaction raw material and the other (or a second) reaction raw material and an outer container installed outside the inner reactor, wherein the inner reactor is made of a material which is substantially resistant to the reaction, the outer container is made of a material which is substantially resistant to at least said one (or the first) reaction raw material, both of the inner reactor and the outer container are arranged so as to keep a gap between them to hold said one (or the first) reaction raw material, and the reaction apparatus is further provided with a supplier for supplying said one (or the first) reaction raw material to the inner reactor and a supplier for supplying the other (or the second) reaction raw material to the inner reactor. The reaction apparatus is preferably employed to carry out the method for producing the hydrogen-containing fluorinated hydrocarbon of the present invention as described above.

In one embodiment of the reaction apparatus according to the present invention, the supplier for supplying said one (or the first) reaction raw material to the inner reactor may be, for example, as described below with reference to FIG. 1, an overflow structure or a pump for supplying said one reaction raw material to the inner reactor through the gap from its source.

In other embodiment of the reaction apparatus according to the present invention, the supplier for supplying the other reaction raw material to the inner reactor may be, for example, as described below with reference to FIG. 1, a pump which supplies it through a pipe which is inserted into the reaction mixture within the inner reactor. In this embodiment, the reaction mixture held in the inner reactor can be mixed without an additional means so as to achieve a further high reaction efficiency.

In a preferred embodiment, the reaction apparatus of the present invention may further comprise a heater which supplies heat to the reaction mixture in order to gasify a fraction which contains the reaction product so as to take out the fraction. Such a heater may be for example, as described below with reference to FIG. 1, a jacket type heat exchanger. The reaction apparatus of the present invention may also be connected to a condensing means (a condenser or the like) to make the gasified and taken-out fraction into a liquid state. Furthermore, the fraction may be subjected to a distillation process, if necessary, in order to divide the fraction taken out of the reaction apparatus and containing the reaction product into respective components, or in order to separate the aimed reaction product.

One embodiment of the present invention will be described below with reference to the drawings. FIG. 1 illustrates a reaction apparatus as one embodiment of the present invention. Employing the reaction apparatus, the method for producing the hydrogen-containing fluorinated hydrocarbon according to the present invention is carried out. In the embodiment illustrated in FIG. 1, liquid-state hydrogen fluoride (HF) is used as one reaction raw material and a halogenated hydrocarbon is used as the other reaction raw material.

The reaction apparatus 20 comprises an inner reactor 2 for carrying out the reaction of said one (or the first) reaction raw material and said other (the second) reaction raw material as well as an outer container 1 installed outside the inner reactor 2. The inner reactor 2 is made of a material which is substantially resistant to the reaction (or the reaction mixture under the reaction conditions), for example, a corrosion resistant metal material, and the outer container 1 is made of a material which is substantially resistant to said one reaction raw material, for example, a metal material. The inner reactor 2 is fixed inside the outer container by means of supports 7 and a gap 3 for holding said one reaction raw material is formed between the outer container 1 and the inner reactor 2.

The outer container 1 and the inner reactor 2 are constructed so as to have an overflow structure, which functions as a means for supplying said one reaction raw material to the inner reactor 2. The overflow structure supplies said one reaction raw material to the inner reactor 2 from the gap 3 (in the direction shown with a dotted line arrow in FIG. 1). The means for supplying said one reaction raw material to the inner reactor 2 is not limited to the overflow structure and may be a pump "P" as schematically illustrated with a dashed line in FIG. 1. Alternatively, while said one reaction raw material is held in the gap 3, said one reaction raw material may newly be supplied directly to the inner reactor 2 from a supply source (e.g. a tank) which is located outside the reaction apparatus.

Figure 1:
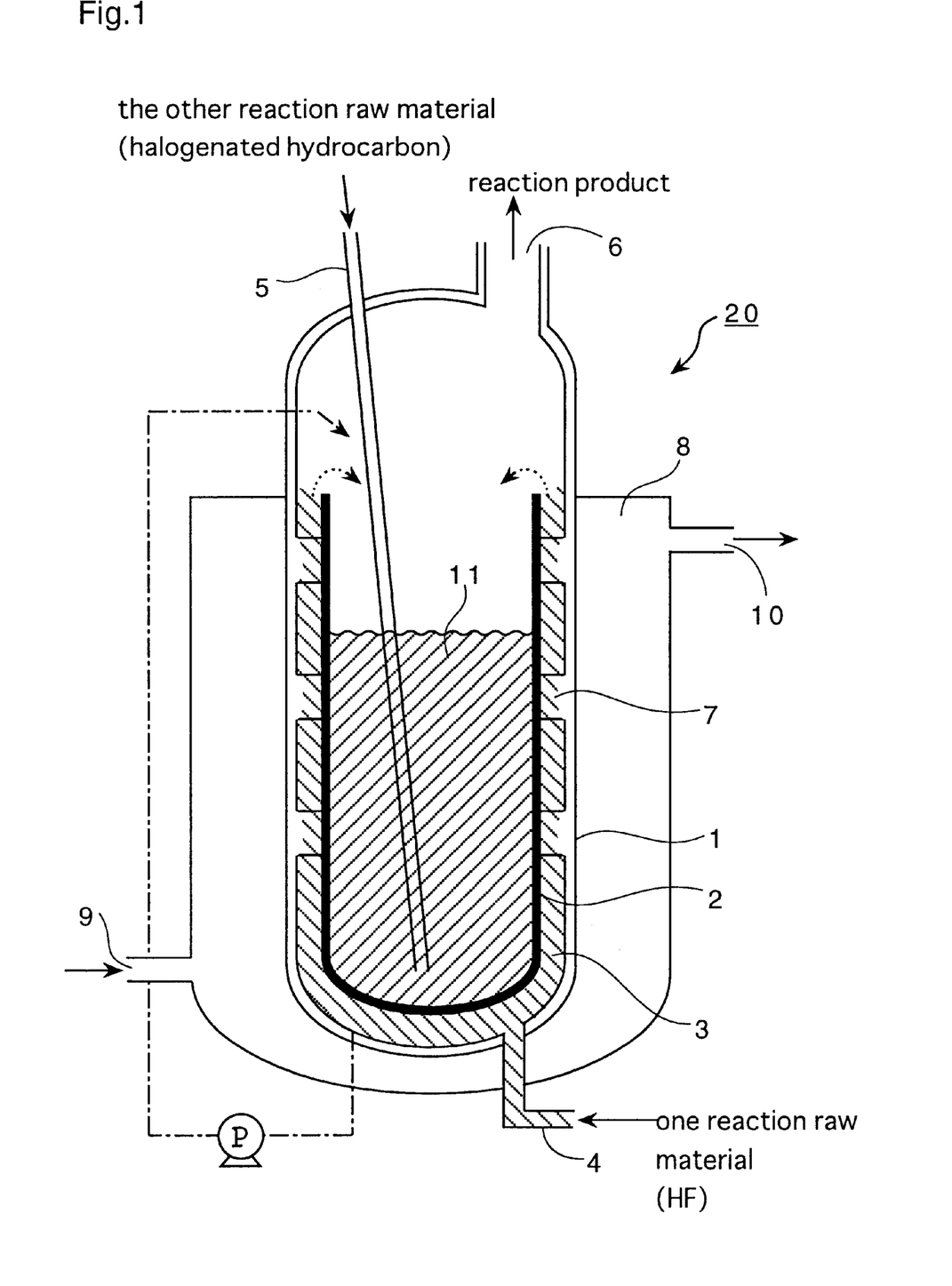
FIG. 1 schematically shows a cross sectional view which illustrates one embodiment of the present invention.

As being illustrated in FIG. 1, an introduction conduit 4 for supplying said one reaction raw material to the gap 3 and an outlet port (or a discharge pipe) 6 for taking out a fraction which contains the reaction product are installed in the outer container 1. As a means for supplying the other reaction raw material to the inner reactor 2, an inserted pipe (an introduction pipe) 5 is installed so as to penetrate the outer container 1 and reach the inside of the inner reactor 2. The pipe 5 is preferably inserted into the reaction mixture 11. Further, as a means for supplying heat to the reaction mixture 11 and gasifying a fraction containing the reaction product, a jacket type heat exchanger 8 having a heating medium inlet 9 and a heating medium outlet 10 is attached to the outside of the outer container 1.

The other reaction raw material to be supplied through the inserted pipe 5 may be in a liquid state or in a gaseous state. By supplying the other reaction raw material to the reaction mixture 11 while using the inserted pipe 5, the reaction mixture 11 can be mixed so that the reaction efficiency may be improved. Alternatively, a stirrer or a mixing device may be installed in the inside of the inner reactor 2 so as to stir or mix the reaction mixture 11.

Next, the method for continuously producing the hydrogen-containing fluorinated hydrocarbon using the above described reaction apparatus 20 will be described below. At first, the inner reactor 2 is previously loaded with the fluorination catalyst (not shown) and liquid state hydrogen fluoride (HF) is supplied to the lower part of the gap between the outer container 1 and the inner reactor 2 through the introduction conduit 4. The supplied hydrogen fluoride overflows into the inner reactor 2 as shown with the dotted line arrow in FIG. 1. On the other hand, the halogenated hydrocarbon as the reaction raw material is directly supplied to the inner reactor 2 through the inserted pipe 5.

Said one reaction raw material (in this embodiment, hydrogen fluoride) and the other reaction raw material (in this embodiment, the halogenated hydrocarbon) introduced as described above are subjected to the fluorination reaction conditions in the inner reactor 2 in the presence of the fluorination catalyst to obtain the reaction mixture containing the hydrogen-containing fluorinated hydrocarbon as the reaction product. The reaction mixture 11 containing at least the reaction product formed by the fluorination reaction is heated by the jacket type heat exchanging apparatus 8. Owing to the heating, the fraction containing a gasified reaction product is taken out through the outlet port 6 installed in the outer container 1 and consequently, the hydrogen-containing fluorinated hydrocarbon as the aimed reaction product can be obtained.

In the embodiment illustrated in FIG. 1, the heat supply to the reaction mixture is carried out by passing a heating medium from the heat medium inlet 9 to the heat medium outlet 10 of the jacket type heat exchanging apparatus 8 and thereby transmitting the heat released from the heat exchanging apparatus 8 to the outer container 1 and in turn to said one reaction raw material held in the gap 3 and then to the reaction mixture 11 through a wall of the inner reactor 2. Hence, it is preferable to use the foregoing metal materials having a high thermal conductivity as described above as the materials for the outer container 1 and preferably also for the inner reactor 2.

The fluorination reaction itself has been already well known and the reaction conditions (the temperature, the pressure, and the supply amounts of the catalyst and the reaction raw materials) can easily be selected by those skilled in the art. For example, see "ADVANCES IN FLUORINE CHEMISTRY", vol. 3, (1963).

The reaction apparatus of the present invention as described above is suitable to carry out the method for producing the hydrogen-containing fluorinated hydrocarbon as described above, however the apparatus is not restricted to the use for such production, but can be used for carrying out other reactions which produces a reaction mixture with extremely high corrosive property.

Figure 2:
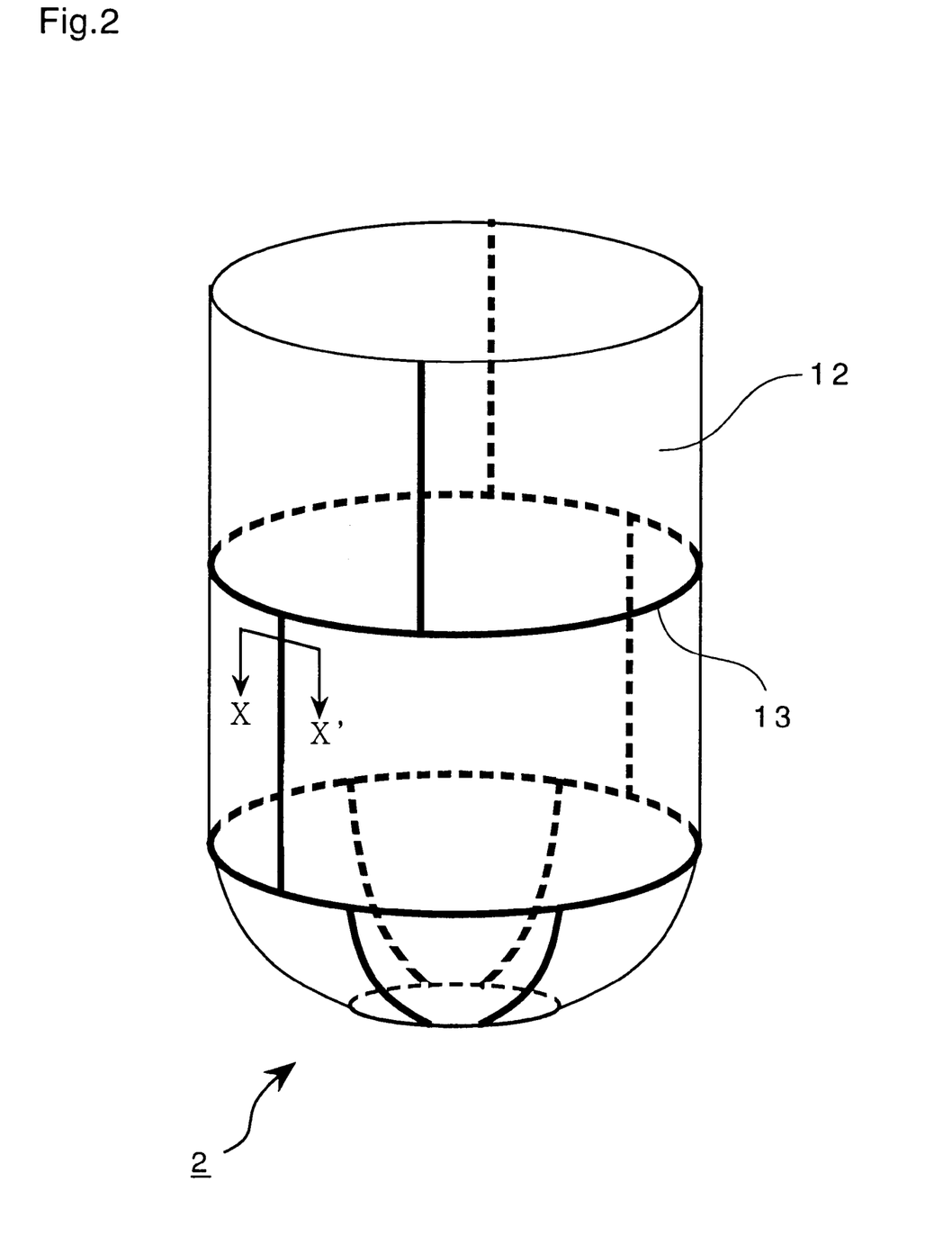
FIG. 2 schematically shows a perspective view of an inner reactor used in one embodiment of the present invention, illustrating joints of the inner reactor.
Figure 3:
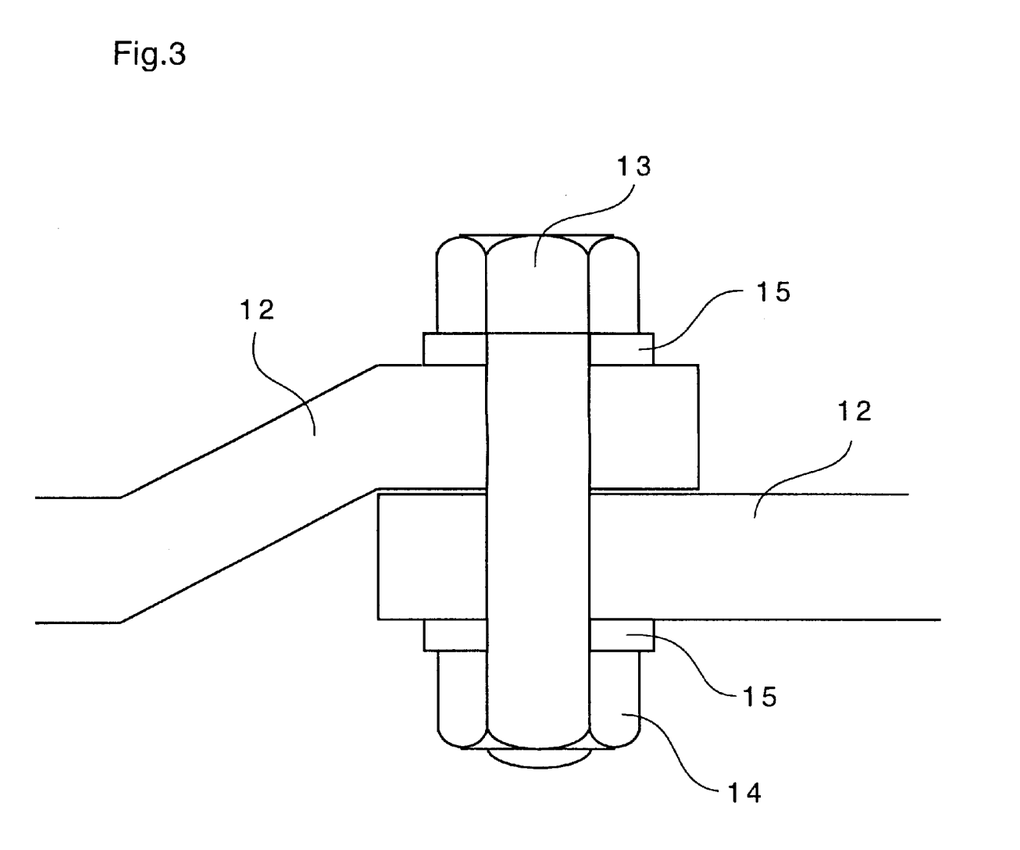
FIG. 3 schematically shows an enlarged partial cross sectional view of a joint of the inner reactor taken along the line X–X' in FIG. 2.

Next, a manner for joining upon manufacturing the inner reactor in which molybdenum is used as a material for the inner reactor 2 will be described with reference to FIGS. 2 and 3. FIG. 2 shows a schematic perspective view of the inner reactor, and FIG. 3 shows a partially magnified cross-sectional view of a joined part of the inner reactor along a line X–X' as illustrated in FIG. 2. The inner reactor 2 of FIG. 2 is manufactured by joining using commercially available plate materials 12 made of molybdenum. In FIG. 2, the plate materials 12 are joined to one another in the joined parts 13. A bolt and nut fixation manner as illustrated in FIG. 3 is employed as the joining manner. The plate materials 12 made of molybdenum are joined to one another by the bolt 13 and the nut 14. Sealing materials 15 are provided between each of the plate materials 12 and the bolt 13 and the nut 14 to improve the seal of the joined part. The Inner reactor manufactured using the joining manner as described above does not always provide sufficient seal because sealing between the adjacent plate materials 12 is not completely carried out. However, as described above, even if the reaction mixture leaks into the gap which is located outside the inner reactor, the reaction mixture is diluted with liquid state hydrogen fluoride in the gap, so that the outer container is not necessarily required to have high corrosion resistance.

EXAMPLES

Example 1

A reaction apparatus 20 having the foregoing structure described with reference to FIGS. 1 to 3 was used, in which molybdenum was used for the material of the inner reactor 2 and iron was used for the material of the outer container 1. The reaction apparatus 20 had a capacity of 500 liters. 30 Kg ($1 \times 10^2$ mol) of $SbCl_5$ as a fluorination catalyst was previously introduced into the inner reactor 2 of the reaction apparatus 20 and 200 liters ($1 \times 10^4$ mol) of liquid-state hydrogen fluoride was also previously introduced into the gap 3 between the outer container 1 and the inner reactor 2.

While the temperature of the reaction mixture 11 in the inside of the inner reactor 2, that is, the reaction temperature, being controlled at 80° C. and the pressure in the reaction apparatus 20, that is, the reaction pressure, being kept at 1.1 MPa (gauge pressure), liquid-state hydrogen fluoride was supplied through the inserted pipe (the introduction pipe) 5 at 16.7 kg/h and liquid-state 1,1,1,3,3-pentachloropropane as a halogenated hydrocarbon was supplied through the introduction pipe 4 at 30 kg/h, whereby liquid-phase fluorination reaction was carried out.

In such a manner just described above, a fraction containing a gaseous reaction product as well as unreacted HF and HCl byproduct was obtained through the outlet port 6. The fraction contained hydrogen-containing fluorinated hydrocarbons (equivalent to about 18 kg/h). The hydrogen-containing fluorinated hydrocarbons contained 99% by mole or higher of 1,1,1,3,3-pentafluoropropane as a main product and slight amounts (less than 1% by mole) of 1,1,1,3-tetrafluoro-3-chloropropane and 1,1,1-trifluoro-3,3-dichloropropane as byproducts.

After the reaction was continued for 500 hours under the above described conditions, the outer container 1 was investigated as to the corrosion by eye observation and corrosion of the outer container was not found at all.

Example 2

A reaction apparatus which is substantially the same as the reaction apparatus used in Example 1 was used, which is also applicable to Examples 3 to 5 unless otherwise indicated.

36 Kg ($1 \times 10^2$ mol) of $TaCl_5$ as a fluorination catalyst was previously introduced into the inner reactor and 200 liters ($1 \times 10^4$ mol) of liquid-state hydrogen fluoride was, as in Example 1, also previously introduced into the gap. Then, while the reaction temperature being controlled at 80° C. and the reaction pressure being kept at 1.1 MPa (gauge pressure) as in Example 1, liquid-state hydrogen fluoride was supplied through the inserted pipe 5 (see FIG. 1) at 39.2 kg/h and liquid-state 1,1,1,2,3,3-hexachloropropene as a halogenated hydrocarbon was supplied through the introduction pipe 4 (see FIG. 1) at 34.5 kg/h, whereby liquid-phase fluorination reaction was carried out.

In such a manner just described above, a fraction which contained hydrogen-containing fluorinated hydrocarbons (equivalent to about 27.5 kg/h) was obtained. The hydrogen-containing fluorinated hydrocarbons contained 99% by mole or higher of 1,1,1,3,3-pentafluoro-2,3-dichloropropane as a main product and a slight amount (less than 1% by mole) of 1,1,1,3-tetrafluoro-2,3,3-trichloropropane as a byproduct.

After the reaction was continued for 500 hours under the above described conditions, the outer container was investigated as to the corrosion by eye observation and corrosion of the outer container was not also found at all also in this Example.

Example 3

As similarly to Example 1, 30 kg ($1 \times 10^2$ mol) of $SbCl_5$ as a fluorination catalyst was previously introduced into the inner reactor and 200 liters ($1 \times 10^4$ mol) of liquid-state hydrogen fluoride was also previously introduced into the gap. Then, while the reaction temperature being controlled at 80° C. and the reaction pressure being kept at 1.1 MPa (gauge pressure) as in Example 1, liquid-state hydrogen fluoride was supplied through the introduction pipe 4 (see FIG. 1) at 11.1 kg/h and liquid-state trichlene, i.e. trichloroethylene, as a halogenated hydrocarbon was supplied through the inserted pipe 5 (see FIG. 1) at 18.2 kg/h, whereby liquid-phase fluorination reaction was carried out.

In such a manner just described above, a fraction which contained hydrogen-containing fluorinated hydrocarbons (equivalent to about 15.9 kg/h) was obtained. The hydrogen-containing fluorinated hydrocarbons contained 99% by mole or higher of 1,1,1-trifluoro-2-chloroethane as a main product and a slight amount (less than 1% by mole) of 1,1-difluoro-1,2-dichloroethane as a byproduct.

After the reaction was continued for 500 hours under the above described conditions, the outer container was investigated as to the corrosion by eye observation and corrosion of the outer container was not also found at all also in this Example.

Example 4

As similarly to Example 1, 30 kg ($1 \times 10^2$ mol) of $SbCl_5$ as a fluorination catalyst was previously introduced into the inner reactor and 200 liters ($1 \times 10^4$ mol) of liquid-state hydrogen fluoride was also previously introduced into the gap. Then, while the reaction temperature being controlled at 100° C. and the reaction pressure being kept at 1.5 MPa (gauge pressure), liquid-state hydrogen fluoride was supplied through the inserted pipe 5 (see FIG. 1) at 14.8 kg/h and liquid-state perchloroethylene, i.e. tetrachloroethylene, as a halogenated hydrocarbon was supplied through the introduction pipe 4 (see FIG. 1) at 23.0 kg/h, whereby liquid-phase fluorination reaction was carried out.

In such a manner just described above, a fraction which contained hydrogen-containing fluorinated hydrocarbons (equivalent to about 19.8 kg/h) was obtained. The hydrogen-containing fluorinated hydrocarbons contained 99% by mole or higher of 1,1,1-trifluoro-2,2-dichloroethane as a main product and a slight amount (less than 1% by mole) of 1,1-difluoro-2,3-dichloroethane as a byproduct.

After the reaction was continued for 500 hours under the above described conditions, the outer container was investigated as to the corrosion by eye observation and corrosion of the outer container was not also found at all also in this Example.

Example 5

As similarly to Example 1, 30 kg ($1 \times 10^2$ mol) of $SbCl_5$ as a fluorination catalyst was previously introduced into the inner reactor and 200 liters ($1 \times 10^4$ mol) of liquid-state hydrogen fluoride was also previously introduced into the gap. Then, while the reaction temperature being controlled at 100° C. and the reaction pressure being kept at 1.1 MPa (gauge pressure), the liquid-state hydrogen fluoride was supplied through the inserted pipe 5 (see FIG. 1) at 22.0 kg/h and liquid-state 1,1,2,3,4,4-hexachlorobutadiene as a halogenated hydrocarbon was supplied through the introduction pipe 4 (see FIG. 1) at 36.2 kg/h, whereby liquid-phase fluorination reaction was carried out.

In such a manner just described above, a fraction which contained hydrogen-containing fluorinated hydrocarbons (equivalent to about 26.9 kg/h) was obtained. The hydrogen-containing fluorinated hydrocarbons contained 98% by mole or higher of 1,1,1,4,4,4-hexafluoro-2-chlorobutene as a main product and slight amounts (less than 2% by mole) of butenes as byproducts which were less fluorinated.

After the reaction was continued for 500 hours under the above described conditions, the outer container was investigated as to the corrosion by eye observation and corrosion of the outer container was not also found at all also in this Example.

What is claimed is:

1. A method for producing a hydrogen-containing fluorinated hydrocarbon in which hydrogen fluoride as a reaction raw material and at least one halogenated hydrocarbon as a reaction raw material selected from a group consisting of a chlorinated alkene and a hydrogen-containing chlorinated alkane are reacted in the presence of a fluorination catalyst so as to obtain a reaction mixture comprising a reaction product which comprises the hydrogen-containing fluorinated hydrocarbon, which method comprises the steps of:
   (a) supplying one of the reaction raw materials to a gap between an inner reactor made of a material which is substantially resistant to the reaction and an outer container made of a material which is substantially resistant to at least said one of the reaction raw materials and which is installed outside the inner reactor;
   (b) supplying said one of the reaction raw materials to the inner reactor;
   (c) supplying the other reaction raw material to the inner reactor; and
   (d) reacting said one of the reaction raw materials with the other reaction raw material in the presence of the fluorination catalyst in the inner reactor so as to obtain the reaction product comprising the hydrogen-containing fluorinated hydrocarbon.

2. The method according to claim 1, wherein the step which supplies said one of reaction raw materials to the gap is continuously carried out, and the step which supplies said one of the reaction raw materials to the inner reactor is continuously carried out by supplying said one of the reaction raw materials from the gap to the inner reactor.

3. The method according to claim 1, wherein the method further comprises the step of obtaining a fraction comprising a gasified reaction product by supplying heat to the reaction mixture followed by withdrawing the fraction.

4. The method according to claim 1, wherein said one of the reaction raw materials is hydrogen fluoride and the other reaction raw material is the halogenated hydrocarbon.

5. The method according to claim 1, wherein said one of the reaction raw materials is the halogenated hydrocarbon and the other reaction raw material is hydrogen fluoride.

6. The method according to claim 1, wherein the fluorination catalyst is at least one compounds selected from a group consisting of $SbF_5$, $SbCl_5$, $SbCl_2F_3$, $NbClF_4$, $NbF_5$, $TaCl_5$, $TaF_5$, and $TaClF_4$.

7. The method according to claim 1, wherein the halogenated hydrocarbon is a chlorinated ethylene which is expressed by the following general formula (1):

$$C_2H_aF_bCl_c \tag{1}$$

wherein a, b, and c are integers satisfying a+b+c=4; a≧0; b≧0, and c≧1.

8. The method according to claim 1, wherein the halogenated hydrocarbon is a hydrogen-containing chlorinated methane which is expressed by the following general formula (2):

$$CH_dF_eCl_f \tag{2}$$

wherein d, e, and f are integers satisfying d+e+f=4; d≧1; e≧0, and f≧1.

9. The method according to claim 1, wherein the halogenated hydrocarbon is a hydrogen-containing chlorinated ethane which is expressed by the following general formula (3):

$$C_2H_gF_hCl_i \tag{3}$$

wherein g, h, and i are integers satisfying g+h+i=6; g≧1; h≧0, and i≧1.

10. The method according to claim 1, wherein the halogenated hydrocarbon is a hydrogen-containing chlorinated propane which is expressed by the following general formula (4):

$$C_3H_jF_kCl_l \tag{4}$$

wherein j, k, and l are integers satisfying j+k+l=8; j≧1; k≧0, and l≧1.

11. The method according to claim 1, wherein the halogenated hydrocarbon is a chlorinated propane which is expressed by the following general formula (5):

$$C_3H_mF_nCl_o \tag{5}$$

wherein m, n, and o are integers satisfying m+n+o=6; m≧0; n≧0, and o≧1.

12. The method according to claim 1, wherein the halogenated hydrocarbon is a chlorinated butadiene which is expressed by the following general formula (6):

$$C_4H_pF_qCl_r \tag{6}$$

wherein p, q, and r are integers satisfying p+q+r=6; p≧0; q≧0, and r≧1.

13. The method according to claim 7, wherein the halogenated hydrocarbon is tetrachloroethylene and the hydrogen-containing fluorinated hydrocarbon is 2,2-dichloro-1,1,1-trifluoroethane.

14. The method according to claim 7, wherein the halogenated hydrocarbon is trichloroethylene and the hydrogen-containing fluorinated hydrocarbon is 2-chloro-1,1,1-trifluoroethane.

15. The method according to claim 8, wherein the halogenated hydrocarbon is dichloromethane and the hydrogen-containing fluorinated hydrocarbon is difluoromethane.

16. The method according to claim 10, wherein the halogenated hydrocarbon is a substituted propane selected from a group consisting of 1,1,1,3,3-pentachloropropane and a partially fluorinated compound thereof and the hydrogen-containing fluorinated hydrocarbon is 1,1,1,3,3-pentafluoropropane.

17. The method according to claim 11, wherein the halogenated hydrocarbon is a substituted propene selected from a group consisting of 1,1,1,2,3,3-hexachloropropene and partially fluorinated compound thereof and the hydrogen-containing fluorinated hydrocarbon is 2,3-dichloro-1,1,1,3,3-pentafluoropropane.

18. The method according to claim 12, wherein the halogenated hydrocarbon is 1,1,2,3,4,4-hexachlorobutadiene and the hydrogen-containing fluoriratedhydrocarbon is 2-chloro-1,1,1,4,4,4-hexafluorobutene.

19. The method according to claim 1 wherein an apparatus comprising an inner reactor in which a reaction of one reaction raw material with the other reaction raw material is carried out, an outer container installed outside of the inner reactor, a supplier which supplies said one reaction material to the inner reactor and a supplier which supplies said the other reaction material to the inner reactor is used, wherein the inner reactor is made of a material which is substantially resistant to the reaction, the outer container is made of a material which is substantially resistant to at least said one reaction raw material, and both of the inner reactor and the outer container are arranged so as to keep a gap between them to hold said one reaction raw materials in the gap.

* * * * *

UNITED STATES PATENT AND TRADEMARK OFFICE
CERTIFICATE OF CORRECTION

PATENT NO. : 6,329,560 B2
DATED : December 11, 2001
INVENTOR(S) : Nakada et al.

It is certified that error appears in the above-identified patent and that said Letters Patent is hereby corrected as shown below:

<u>Title page,</u>
Under Item [56], References Cited, please add -- M. Stacey et al., "Advances in Fluorine Chemistry", Washington, Vol. 3, pp. 188-217 (1963). --

Signed and Sealed this

Fourth Day of June, 2002

*Attest:*

*Attesting Officer*

JAMES E. ROGAN
*Director of the United States Patent and Trademark Office*